United States Patent [19]

Green

[11] Patent Number: 4,529,587

[45] Date of Patent: Jul. 16, 1985

[54] METHOD OF REDUCING SEBUM ON THE HAIR AND SKIN

[75] Inventor: Martin R. Green, Milton Keynes, United Kingdom

[73] Assignee: Lever Brothers Company, New York, N.Y.

[21] Appl. No.: 462,859

[22] Filed: Feb. 1, 1983

[30] Foreign Application Priority Data

Feb. 19, 1982 [GB] United Kingdom ............... 8204958

[51] Int. Cl.³ .................... A61K 7/06; A61K 7/07; A61K 31/42

[52] U.S. Cl. ........................ 424/70; 424/DIG. 4; 424/47; 424/59; 424/60; 424/65; 424/67; 424/68; 424/69; 514/770; 514/784; 514/778; 514/769; 514/387; 514/781; 514/846

[58] Field of Search .............. 424/69, 70, 47, DIG. 4, 424/273 R, 273 B; 548/126

[56] References Cited

U.S. PATENT DOCUMENTS

| 2,370,662 | 3/1945 | Hertz et al. | 424/95 X |
|---|---|---|---|
| 3,879,534 | 4/1975 | Rambacher et al. | 424/DIG. 4 |
| 4,243,655 | 1/1981 | Gunther | 424/273 R |

FOREIGN PATENT DOCUMENTS 2746650  4/1979  Fed. Rep. of Germany ...... 514/770

OTHER PUBLICATIONS

Vanderwyke et al., J. Soc. Cos. Chemists, 9/1967, vol. 18, pp. 629–639.

*Primary Examiner*—Dale R. Ore
*Attorney, Agent, or Firm*—Lynne Darcy; James J. Farrell

[57] ABSTRACT

A cosmetically acceptable composition for topical application to human skin or hair in order to reduce greasiness comprises, at a concentration of from 0.0001M to 0.5M, a biotin antagonist which is capable of blocking the activity of the biotin dependent enzyme acetyl-SCoA-carboxylase implicated in sebum production; together with a carrier other than water as an aid to delivering the biotin antagonist to the sebaceous gland.

19 Claims, No Drawings

METHOD OF REDUCING SEBUM ON THE HAIR AND SKIN

The invention relates to cosmetic compositions for topical application to the skin or hair, particularly to compositions that are effective in reducing the amount of sebum which normally accumulates on the skin surface.

Normal healthy skin scretes a natural lubricant known as sebum, which usually serves to keep the skin surface soft, pliable, conditioned and, to some extent, protected.

Sebum, a complex mixture of lipid substances, is secreted from sebaceous glands associated with hair follicles over most of the body surface, in particular the scalp, face, upper chest and shoulders.

Normal healthy human skin also secretes sweat from eccrine and apocrine glands. Eccrine sweat is associated with both the control of body temperature and the secretion of waste products: it consists mainly of water but contains also inorganic and organic components, notably sodium chloride and lactic acid. Apocrine sweat is associated with adrenergic stimulus and in addition to water and sodium chloride, also contains odour producing proteins, lipoproteins and lipids.

Whereas the secretion at the skin surface of sebum and sweat represents a normal and necessary bodily function, excessive production of these secretions can result in a film on the skin surface which is oily or greasy in nature and which can be disliked to the extent that the human subject will go to considerable trouble to remove it, for example by tissue wiping, by excessive washing or by application of make-up, so as to block skin pores from which sebum and sweat are released onto the skin surface.

The control of lipids secreted onto the skin, to provide a proper balance whereby the skin remains supple and protected yet without being excessively greasy, has accordingly presented a problem to the cosmetician, and hitherto it has been difficult in a non-clinical environment to strike the proper balance by the simple application of a topical product. In any case, efforts in this direction have concentrated solely on the removal of excess sebum after secretion onto the skin surface.

It has, however, now been discovered that, by topical application to skin or hair of one or more special biotin anatagonists dissolved in a suitable liquid carrier, the synthesis of sebum in the sebaceous glands can be suppressed so that a reduced amount of sebum is secreted onto the skin surface.

It has been proposed by Gunther in U.S. Pat. No. 4,243,655 to employ very low concentrations of biotin antagonists in products such as toothpastes and mouthwashes for oral use. Gunther observed that many of the microorganisms implicated in the production of dental caries require an outside source of biotin, usually present in saliva, and hence by blocking biotin uptake by application of a large excess of a biotin antagonist, conditions are make unfavourable for plaque and acid formation by the oral microflora. The concentrations of biotin antagonists advocated by Gunther were 0.00056% by weight for toothpastes, and 0.00004% by weight for mouthwashes, and 0.0011% for toothpowder.

We have shown that topically applied compositions containing as little as 0.002% by weight of a biotin antagonist are insufficient to influence sebum production and that a higher concentration of these materials is accordingly required before any significant reduction in sebum production is observed.

By "biotin antagonist" is meant any compound which can inhibit the biological function of biotin.

While studying the effect of biotin antagonists on sebum secretion, it was discovered that most of the biotin occurring naturally in skin is located in the sebaceous glands. It has also been noted that a biotin dependent enzyme, acetyl-SCoA-carboxylase, involved in lipid synthesis is located in the sebaceous gland, and that its activity can be impaired by the introduction of biotin antagonists. Hence the synthesis of lipids in the sebaceous glands is reduced and consequently the skin surfaces where sebaceous glands are found are less greasy.

The role of biotin in the function of acety-SCoA-carboxylase, the inactivation of this enzyme with biotin antagonists and evidence to support the interference by biotin antagonists of skin lipid synthesis will be outlined later in this specification.

The invention is accordingly concerned with the topical application of biotin antagonist at a concentration sufficient to block the activity of biotin dependent enzymes located in the sebaceous gland which are implicated in lipid synthesis.

More particularly, the invention provides a cosmetically acceptable composition for topical application to human skin or hair which comprises, at a concentration of from 0.0001M to 0.5M, a biotin antagonist or a salt thereof, which is capable of blocking the activity of the biotin dependent enzyme acetyl-SCoA-carboxylase; together with a carrier other than water.

Any cosmetically acceptable biotin antagonist can be employed in the composition to block the activity of acetyl-SCoA-carboxylase and so reduce sebaceous lipid synthesis.

A preferred class of biotin antagonists is that having the structure (I):

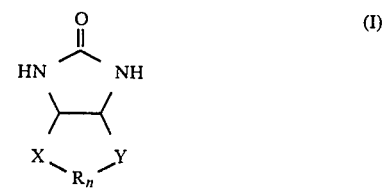

where n is zero or 1 and
when n is zero,
X is —CH₃, and
Y is —(CH₂)ₘZ, and
when n is 1,
R is chosen from >O, >S, >S=O and

X is >CH₂, and Y is >CH(CH₂)ₘ₋₁Z, where
m is an integer of from 1 to 8, and
Z is chosen from —CH₂COOH, —CH=CH-COOH, —CH(CH₃)COOH, —CH₂COOCH₃, —NHNH₂ and —SO₃H
provided that when R is >S and Z is —CH₂COOH, then m is an integer of from 1 to 3 or 5 to 8.

Examples of biotin antagonists having the structure (I) where n is zero and where Z is —CH₂COOH are:

trisnordesthiobiotin, where m is 1,
bisnordesthiobiotin, where m is 2,
nordesthiobiotin, where m is 3,
desthiobiotin, where m is 4,
homodesthiobiotin, where m is 5
bishomodesthiobiotin, where m is 6,
trishomodesthiobiotin, where m is 7, and
tetrahomodesthiobiotin, where m is 8.

Further examples of biotin antagonists having the structure (I) where n is 1 and where R is >S=O and where Z is —CH₂COOH are:

trisnorbiotin sulphoxide, where m is 1,
bisnorbiotin sulphoxide, where m is 2,
norbiotin sulphoxide, where m is 3,
biotin sulphoxide, where m is 4,
homobiotin sulphoxide, where m is 5,
bishomobiotin sulphoxide, where m is 6, and
trishomobiotin sulphoxide, where m is 7.

Further examples of biotin antagonists having the structure (I) where n is 1 and where

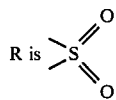

and where Z is —CH₂COOH are:

trisnorbiotin sulphone, where m is 1,
bisnorbiotin sulphone, where m is 2,
norbiotin sulphone, where m is 3,
biotin sulphone, where m is 4,
homobiotin sulphone, where m is 5,
bishomobiotin sulphone, where m is 6, and
trishomobiotin sulphone, where m is 7.

Further examples of biotin antagonists having the structure (I) where n is 1 and where R is >S and where Z is —CH₂COOH are:

trisnorbiotin, where m is 1,
bisnorbiotin, where m is 2,
norbiotin, where m is 3,
homobiotin, where m is 5,
bishomobiotin, where m is 6, and
trishomobiotin, where m is 7.

A further example of biotin antagonists having the structure (I) where n is 1 and where R is >S and where Z is —CH=CHCOOH is:

α-dehydrobiotin, where m is 3.

A further example of biotin antagonist having the structure (I) where n is 1 and where R is >S and where Z is —CH(CH₃)COOH is:

α-methyl biotin, where m is 4.

Further examples of biotin antagonists having the structure (I) where n is 1, and where R is >O and where Z is —CH₂COOH are:

trisnoroxybiotin, where m is 1,
bisnoroxybiotin, where m is 2,
noroxybiotin, where m is 3,
oxybiotin, where m is 4,
homooxybiotin, where m is 5,
bishomooxybiotin, where m is 6, and
trishomooxybiotin, where m is 7.

Futher examples of biotin antagonists having the structure (I) where n is 1 and where R is >O and where Z is —SO₃ are:

trisnoroxybiotin sulphonic acid, where m is 2,
bisnoroxybiotin sulphonic acid, where m is 3,
noroxybiotin sulphonic acid, where m is 4,
oxybiotin sulphonic acid, where m is 5,
homooxybiotin sulphonic acid, where m is 6,
bishomooxybiotin sulphonic acid, where m is 7,
trishomooxybiotin sulphonic acid, where m is 8.

Further examples of biotin antagonists having the structure (I) and where n is 1 and R is >S and where Z is —CH₂COOCH₃ are:

trisnorbiotin methyl ester, where m is 1,
bisnorbiotin methyl ester, where m is 2,
norbiotin methyl ester, where m is 3,
biotin methyl ester, where m is 4,
homobiotin methyl ester, where m is 5,
bishomobiotin methyl ester, where m is 6,
trishomobiotin methyl ester, where m is 7,
tetrahomobiotin methyl ester, where m is 8.

Further examples of biotin antagonists having the structure (I) and where n is 1 and

and where Z is —CH₂COOCH₃ are:

trisnorbiotin sulphone methyl ester, where m is 1,
bisnorbiotin sulphone methyl ester, where m is 2,
norbiotin sulphone methyl ester, where m is 3,
biotin sulphone methyl ester, where m is 4,
homobiotin sulphone methyl ester, where m is 5,
bishomobiotin sulphone methyl ester, where m is 6,
trishomobiotin sulphone methyl ester, where m is 7,
tetrahomobiotin sulphone methyl ester, where m is 8.

Further examples of biotin antagonists having the structure (I) where n is 1 and where R is >S and where Z is —NHNH₂ are:

trisnorbiotin hydrazide, where m is 2,
bisnorbiotin hydrazide, where m is 3,
norbiotin hydrazide, where m is 4,
biotin hydrazide, where m is 5,
homobiotin hydrazide, where m is 6,
bishomobiotin hydrazide, where m is 7,
trishomobiotin hydrazide, where m is 8.

A further class of biotin antagonists is that having the structure (II):

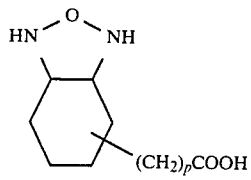

(II)

where p is 2 to 5

Specific examples of biotin antagonists having the structure (II) are:

γ-(2,3-ureylenecyclohexyl)butyric acid, where p is 3
δ-(2,3-ureylenecyclohexyl)valeric acid, where p is 4,
γ-(3,4-ureylenecyclohexyl)butyric acid, where p is 3, and
δ-(3,4-ureylenecyclohexyl)valeric acid, where p is 4.

Examples of other biotin antagonists are:

2-oxo-4-imidazolidine caproic acid, thiazolidine,
methyl-1,3-acetyl-4-thiazolidine carboxylate,
1,2-propyl-2-acetyl-4-thiazolidine carboxylate methyl ester and its hydrazide,
2-piperidone-6-carboxylic acid hydrazide,
α-(2-carboxy-3-indolyl)butyric acid hydrazide,
2-imidazoline-4-carboxylic acid hydrazide,
2-imidazoline-4-caproic acid hydrazide,
2-imidazoline-4-valeric acid hydrazide,
ureylenetetrahydrofuryl aliphatic sulphonic acids, benzyl thioethers,
semicarbazides of biotin, and
bishydrazides of suberic and sebacic acids.

It is to be understood that the above examples of biotin antagonists include all possible sterioisomers as appropriate.

The most preferred biotin antagonists for use in compositions according to the invention are:

biotin sulphone,
biotin sulphone methyl ester,
α-dehydrobiotin,
biotin hydrazide,
homobiotin,
homobiotin methyl ester.

A biotin antagonist can be used alone in the composition or in admixture with one or more other biotin antagonists and/or biotin antagonist salts.

The biotin antagonists should be present in the composition in an amount which will effectively decrease the activity of the enzyme acetyl-SCoA-carboxylase and hence reduce the lipid synthesis in the sebaceous glands so that less sebum is produced. The composition should accordingly comprises a biotin antagonist at a concentration of from 0.0001M to 0.5M, preferably from 0.001M to 0.1M and most preferably from 0.01M to 0.1M.

It is apparent that if the composition contains the biotin antagonist at a concentration of less than 0.0001M, then the secretion of sebum at the skin surface is unlikely to be reduced, whereas if the composition contains the biotin antagonist at a concentration of more than 0.5M, then it is unlikely that any extra benefit in terms of reduction of sebum secretion at the skin surface will be apparent compared with that obtained using a composition in which the biotin antagonist is present at a concentration of 0.5M.

Expressed in terms of weight percentage, the biotin antagonist should form from about 0.004% to about 10%, preferably 0.03% to 2%, most preferably 0.2% to 2% by weight of the composition.

The composition should also comprise a carrier other than water to enable the biotin antagonist to be conveyed to the sebaceous gland.

The selection of a carrier for biotin antagonists in compositions of the invention presents a wide range of possibilities depending on the required product form of the composition. Suitable carriers can be classified as described hereinafter.

It should be explained that carriers are substances which can act as diluents, dispersants, or vehicles, as well as solvents for biotin antagonists, and which therefore ensure that they can be applied to and distributed evenly over the skin at an appropriate concentration; the carrier is preferably one which can aid penetration of the biotin antagonist into the sebaceous glands, thus ensuring that the effectiveness of the applied biotin antagonists is prolonged because of improved substantivity. Compositions according to this invention can include water, which can act as a carrier, provided that there is also present at least one cosmetically acceptable carrier other than water.

Carriers other than water that can be used in compositions according to the invention can include solids or liquid such as emollients, propellants, solvents, humectants, thickeners and powders. Examples of each of these types of carriers, which can be used singly or as mixtures of one or more carriers, are as follows:

Emollients, such as stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcholol, cetyl palmitate, dimethylpolysiloxane, di-n-butyl sebacate, isopropyl myristate, isopropyl palmitate, isopropyl stearate, butyl stearate, polyethylene glycol, triethylene glycol, lanolin, castor oil, acetylated lanolin alcohols, petrolatum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluorothane, monochlorodifluoromethane, trichlorotrifluoroethane propane, butane, isobutane, dimethyl ether, carbon dioxide, nitrous oxide;

Solvents, such as ethyl alcohol, methylene chloride, isopropanol, castor oil, ethylene glycol monoethyl ether, diethylene glycol monobutyl ether, diethylene glycol monoethyl ether;

Humectants, such as gylcerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate.

The preferred carrier is a lower alkanol, preferably a $C_1$ to $C_4$ alkanol.

The most preferred $C_1$ to $C_4$ to alkanol is ethanol or isopropanol or a mixture thereof.

The amount of carrier in the composition, including water if present, should preferably be sufficient to carry at least a portion of the biotin antagonist to the sebaceous gland which is sufficient effectively to reduce sebum secretion onto the skin surface. The amount of liquid carrier can comprise the major portion of the composition, particularly where little or no other ingredients are present in the composition.

The composition will accordingly comprise from 50 to 99.996% and preferably from 90 to 99.5% by weight of the carrier or carriers.

The compositions according to the invention can contain ingredients other than those already mentioned, depending on the form of the intended product. It is, for example, possible to include antiseptics, preservatives antioxidants, emulsifiers, perfumes, colouring agents and detergents.

The composition according to the invention can also be employed as a vehicle for a wide variety of cosmetically or pharmaceutically active ingredients, particularly ingredients which have some beneficial effect when applied to the skin or hair.

The composition thus provides a means whereby such active ingredients can be diluted, dispersed, conveyed to and distributed on the skin surface or on the hair at an appropriate concentration.

Especially preferred examples of active ingredients include moisturisers, anti-acne agents, sunscreen agents, germicides, deodorants, antiperspirants, healing agents and detergents.

The invention also provides a process for the preparation of a cosmetic composition for topical application to skin or hair which comprises mixing a biotin antagonist with a suitable carrier to provide a concentration of from 0.0001M to 0.5M.

The compositions of the invention can be formulated as liquids, for example as a lotion or milk for use in conjunction with an applicator such as a roll-ball applicator, or a spray device such as an aerosol can contaning propellant, or a container fitted with a pump to dispense the liquid product. Alternatively, the compositions of the invention can be solid or semi-solid, for example creams or gels, for use in conjunction with a suitable applicator or simply a tube, bottle or lidded jar.

The invention accordingly also provides a closed container containing a cosmetic composition as herein defined.

Compositions of the invention are intended especially for topical application to human skin or hair, in particular when the skin surface or the hair has become excessively greasy due to an accumulation of sebum.

Topical application of the composition will accordingly reduce the superficial "grease" without unduly defatting the skin. The skin or hair will then remain in a healthy, non-greasy condition, usually for several hours. It can also usefully be employed in the treatment of acne as excess sebum production is a universal accompaniment of acne.

An explanation of the role of biotin in the function of acetyl-SCoA-carboxylase and the inactivation of this enzyme with biotin antagonists Biotin is an essential cofactor for acety-SCoA-carboxylase, an enzyme which converts acety-CoA into malonyl-CoA. This step is thought to determine the rate at which fatty acids, such as palmitate are synthesised in the sebaceous gland from precursors. This synthetic pathway can be illustrated as follows:

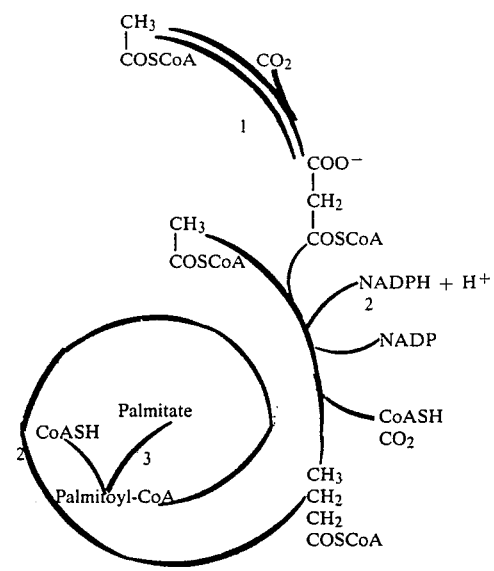

Enzymes involved in fatty acid synthesis
1. Acetyl-SCoA carboxylase
2. Fatty acid synthetase
3. Deacylase Palmitate and other fatty acids are the basic building blocks for triglycerides and provides some of the precursors for wax and sterol esters. These lipid classes make up the bulk of human sebum. Therefore, it can be seen that inhibition of the enzyme acetyl-SCoA-carboxylase, which can be achieved by inhibiting biotin function using biotin antagonists, can significantly reduce the ability of sebaceous glands to synthesise lipids. This will, in turn, deplete the skin surface of lipids and reduce greasiness.

It is believed that at the molecular level, biotin functions to transfer and to help activate carbon dioxide derived from bicarbonate. The carbon dioxide must be transferred precisely from one enzymatic site to another; and be delivered in the correct orientation and state of activation by the biotin attached to the carrier protein as shown above. If this is not achieved, then the enzyme will not function. Hence it can be predicted that small perturbations in the biotin molecule, for example lengthening or shortening the biotin side chain, altering the charge distribution of biotin or altering the shape of the biotin molecule, can render the acetyl-SCoA-carboxylase molecule inactive. Hence a very wide range of analogues of biotin, herein referred to as biotin antagonists, are biologically inactive with respect to the essential requirements of acetyl-SCoA-carboxylase. It can be deduced that any antagonist of biotin function of whatever nature can inhibit the activity of acetyl-SCoA-carboxylase.

Evidence of the effect of biotin antagonists on acetyl-SCoA-carboxylase activity Experiments as described below were carried out using biotin sulphone as an example of a biotin antagonist.

1. In vitro experiments using cultured human fibroblasts

In preliminary experiments the ability of biotin sulphone to reduce the activity of acetyl-SCoa-carboxylase in an in vitro assay was assessed using cultured human dermal fibroblasts as described in Ghneim et al (1981) Biochem. Soc. Trans. 9, 405-6 and references therein. Human dermal fibroblasts were maintained in culture for 3 days with 1 µM biotin sulphone in the presence of a nutrient medium containing 10% foetal calf serum. The level of naturally occurring biotin was about 10 nM. Enzyme activity was assayed in the cell pellet by the fixation of $^{14}$C-sodium bicarbonate into protein in the presence of acety-CoA under appropriate conditions. Control experiments were done in the absence of biotin sulphone and enzyme activities were calculated with respect to protein.

The results obtained are shown Table 1 below:

TABLE 1

|  | nCi $^{14}$C—bicarbonate fixed per mg protein | Acetyl-SCoA-carboxylase activity (%) |
|---|---|---|
| Control | 4.46 | 100 |
| Test (+1 µM biotin sulphone) | 3.26 | 73 |

These results show that there was a 27% reduction in acetyl-SCoA-carboxylase activity as a result of culture in the presence of biotin sulphone. A similar reduction was observed when the results were calculated in terms of nCi $^{14}$C-bicarbonate incorporated into protein per mg of DNA.

2. In vivo experiments using rats

Experimental methodology

Ten, 3 week male weanling rats, clipped on left and right flanks, were divided into two groups of five animals. One group was untreated on the left flank while the right flank received the test solution (1 mg/ml biotin sulphone in 70% ethanol:30% water) twice a day (once per day at weekends) for six weeks. The second group received the ethanol/water carrier on the left flank and the test solution on the right. At the end of the treatment the rats were killed, skin removed and divided approximately into epidermis and dermis using a 0.2 mm keratatome cut. Samples of dermis containing most of the sebaceous tissue from either untreated (UN), vehicle (V) or test (T) treated skin were incubated in a nutrient medium (basal eagles medium +10% foetal calf seru, 20 mM hepes pH 7.4, antibiotics, 100 µM sodium acetate containing 1 µCi/ml sodium (1-$^{14}$C) acetate for 19 hours at 37° C. The $^{14}$C-acetate is metabolically incorporated into lipids and gives a "snap shot" of the lipid synthesis profile over the 19 hour time period. At the end of the incubation samples were washed in ice cold medium without $^{14}$C-acetate, quenched in ice cold 5% trichloroacetic acid (TCA), homogenised and centrifuged to separate insoluble residue from TCA soluble material ("TCA" fraction). The TCA fraction contains nucleo dtides, small metabolites especially succinate, amino acids, small peptides and free $^{14}$C-acetate. Lipids were extracted in chloroform:methanol and subject to Folch washing essentially as described by Prottey el al., Brit. J. Dermatol. (1972) 87, 586-607 generating the following fractions : "lipids", "aqueous methanol" containing only a small proportion of skin lipids with a very low $^{14}$C count and an extracted "solid residue". The total $^{14}$C count in all these fractions was determined.

The radioactive lipids were fractionated into free fatty acids (FFA) monoglycerides (MG), diglycerides (trace only) and triglyerides (TG) using a standard, neutral solvent, thin layer chromatography system.

Results

The following ratio provides a measure of lipid synthesis per unit volume of skin, that is the total $^{14}$C-acetate uptake into lipids (i.e. amount of lipid synthesis) divided by the $^{14}$C-acetate uptake into the remaining tissue fractions (i.e. a measure of sample size). (Remaining tissue="TCA" fraction+"solid residue").

The ratios derived in each of the ten rats are recorded in Table 2 below.

TABLE 2

| | Treatment | |
|---|---|---|
| Rat | CONTROL UN or V ratio | TEST Test ratio |
| A | 0.74 | 0.43 |
| B | 0.94 | 0.23 |
| C | 0.37 | 0.59 |
| D | 0.65 | 0.44 |
| E | 0.58 | 0.52 |
| F | 0.25 | 0.53 |
| G | 0.55 | 0.58 |
| H | 0.63 | 0.39 |
| I | 0.75 | 0.73 |
| J | 0.53 | 0.43 |
| | Av. 0.59 | Av. 0.49   −18% |

Rats A-E received vehicle on their left flank
Rats F-J received no treatment on their left flank The data show that topical application of biotin sulphone has caused an overall 18% reduction in $^{14}$C-acetate uptake into dermal lipids. However $^{14}$C-acetate is also incorporated into the cholesterol synthetic pathway which should be largely unaffected by the biotin sulphone treatment. This will cause a "dilution" of the reduction seen above. Accordingly, the lipids whose synthesis is dependent on acetyl-SCoA-carboxylase have been isolated. These are free fatty acids (FFA), monoglyceride (MG), diglyeride (trace) triglyceride (TG). It is predicted that a greater reduction in the incorporation of $^{14}$C-acetate into "triglyceride" lipid should now be observed. As fatty acids are the primary product made by the acetyl-SCoA-carboxylase pathway in the sebaceous gland, results for this lipid class have been included separately, as well as for total "triglyceride" lipid; values of six of the rats are given in Table 3 below:

TABLE 3

| | Treatment | | | |
|---|---|---|---|---|
| | FFA Synthesis | | "Triglyceride" lipid[b] synthesis | |
| Rat | V + UN | Test | V + UN | Test |
| A | 1[a] | 0.78 | 19.58 | 13.93 |
| B | 3.27 | 0.41 | 41.92 | 8.58 |
| C | 1.12 | 0.60 | 11.41 | 15.17 |
| F | 1.29 | 1.67 | 6.52 | 15.38 |
| G | 1.05 | 0.78 | 14.24 | 14.74 |
| H | 1.27 | 1.22 | 15.74 | 9.85 |
| | Av. 1.50 | Av. 0.91 −39% | Av. 18.24 | Av. 12.94 −29% |

Notes:
[a] = 41,151 DPM $^{14}$C—acetate incorporated into lipid including a correction for sample size, namely the $^{14}$C—acetate uptake into the remaining tissue, as in Table 2.
[b]"Triglyceride" lipid values are the sum of FFA + MG + TG.

The results show that biotin sulphone treatment reduces denovo FFA synthesis by 39% and "Triglyceride" (i.e. FFA+MG+TG) synthesis by 29% confirming the inhibitory action of biotin antagonists on acetyl-SCoA-carboxylase activity and on lipid synthesis in the sebaceous gland. The 29% reduction in FFA+MG+TG sebaceous lipid synthesis closely parallels the 27% drop in acetyl-SCoA carboxylase activity found for the in vitro cell culture assay system suggesting that the biotin sulphone treatment can be equally effective in reducing acetyl-SCoA-carboxylase activity in the cell culture system and in the rat sebaceous gland.

The invention is illustrated by the following examples:

EXAMPLE 1

This Example illustrates a lotion according to the invention which is suitable for topical application to the skin of the face in order to reduce the secretion of sebum at the skin surface.

The lotion has the following formulation:

|  | % w/w |
|---|---|
| biotin sulphone | 0.005 |
| ethanol | 99.995 |
| perfume | q.s. |

EXAMPLE 2

This Example illustrates a hair tonic which is suitable for application to greasy hair or scalp for reducing the accumulation of sebum on the hair or scalp.

The hair tonic has the following formulation:

|  | % w/w |
|---|---|
| biotin sulphone | 0.01 |
| ethanol | 50 |
| water | 49.99 |
| perfume | q.s. |

EXAMPLE 3

This Example also illustrates a lotion which is suitable for topical application to the skin of the face in order to reduce the secretion of sebum at the skin surface.

The lotion has the following formulation:

|  | % w/w |
|---|---|
| homobiotin | 0.015 |
| propan-2-ol | 10 |
| ethanol | 89.985 |
| perfume | q.s. |

EXAMPLE 4

This example also illustrates a hair tonic which is suitable for application to greasy hair or scalp for reducing the accumulation of sebum on the hair or scalp.

The hair tonic has the following formulation:

|  | % w/w |
|---|---|
| α-dehydrobiotin | 0.02 |
| ethanol | 40 |
| water | 59.98 |
| perfume | q.s. |

EXAMPLES 5-8

The following formulations represent lotions which can be used topically in the treatment of greasy and/or acneic skin.

|  | % w/w | | | |
|---|---|---|---|---|
|  | 5 | 6 | 7 | 8 |
| Hydroxyethyl cellulose | 0.4 | — | 0.4 | — |
| Absolute ethanol | 25 | 25 | 25 | 25 |
| Propane-1,2-diol | — | — | 38.4 | 38.4 |
| Butane-1,3-diol | 38.4 | 38.8 | — | — |
| Paramethyl benzoate | 0.2 | 0.2 | 0.2 | 0.2 |
| bisnordesthiobiotin | 0.05 | — | — | — |
| nordesthiobiotin | — | 0.01 | — | — |
| homobiotin | — | — | 0.009 | — |
| homobiotin methyl ester | — | — | — | 0.15 |
| Perfume | 1 | 1 | 1 | 1 |
| Water to | 100 | 100 | 100 | 100 |

EXAMPLE 9-12

The following formulations represent lotions which can be used topically in the treatment of greasy and/or acneic skin.

|  | % w/w | | | |
|---|---|---|---|---|
|  | 9 | 10 | 11 | 12 |
| Ethanol | 10 | 10 | 10 | 10 |
| Propane-1,2-diol | 30 | — | 55 | — |
| Butane-1,3-diol | — | 30 | — | 55 |
| bishomodesthiobiotin | 0.1 | — | — | — |
| trishomodesthiobiotin | — | 0.2 | — | — |
| desthiobiotin | — | — | 0.09 | — |
| homodesthiobiotin | — | — | — | 0.15 |
| perfume | q.s. | q.s. | q.s. | q.s. |
| Water to | 100 | 100 | 100 | 100 |

EXAMPLES 13-16

The following formulations represent creams which can be used in the treatment of greasy skin.

|  | % w/w | | | |
|---|---|---|---|---|
|  | 13 | 14 | 15 | 16 |
| Cetyl alcohol polyoxyethylene (10) | 4 | 4 | 4 | 4 |
| Cetyl alcohol | 4 | 4 | 4 | 4 |
| Mineral oil | 4 | 2 | — | — |
| Paraffin wax | — | 2 | 4 | — |
| Partial glyceride of palmitic and stearic acids | — | — | — | 4 |
| biotin sulphone | — | — | — | 1 |
| homobiotin sulphoxide | 0.1 | — | — | — |
| bishomobiotin sulphoxide | — | 0.15 | — | — |
| trishomobiotin sulphoxide | — | — | 0.2 | — |
| Triethanolamine | 0.75 | 0.75 | 0.75 | 0.75 |
| Butane-1,3-diol | 3 | 3 | 3 | 3 |
| Xanthan gum | 0.3 | 0.3 | 0.3 | 0.3 |
| Preservative | 0.4 | 0.4 | 0.4 | 0.4 |
| perfume | q.s. | q.s. | q.s. | q.s. |
| Water to | 100 | 100 | 100 | 100 |

EXAMPLE 17

The following formulation represents a lotion which can be used in the treatment of greasy and/or acneic skin.

|  | % w/w |
|---|---|
| Butane-1,3-diol | 20 |
| Ethanol | 45 |
| homobiotin sulphone | 0.5 |
| Perfume | q.s. |

EXAMPLE 18

This example illustrates a water-in-oil high internal phase emulsion containing bisnorbiotin sulphone according to the invention.

The emulsion consisted of 10% by volume oily phase and 90% by weight aqueous phase.

The oily phase and the aqueous phase had the following constitution:

|  | % w/w |
|---|---|
| Oily phase |  |
| Sorbitan monooleate | 20 |
| Quarternium-18 hectorite | 5 |
| Liquid paraffin | 75 |
| Aqueous phase |  |
| bisnorbiotin sulphone | 0.5 |
| Xanthan gum | 1 |
| Preservative | 0.3 |
| Perfume | q.s. |
| Sodium chloride (1% w/w solution) to | 100 |

The emulsion was prepared by taking 10 parts by volume of the oily phase and to it adding slowly with stirring 90 parts by volume of the aqueous phase.

The high internal phase water-in-oil emulsion so formed can be applied topically to improve skin condition generally or to alleviate greasiness and in the treatment of acne.

EXAMPLE 19

This example illustrates a water-in-oil high internal phase emulsion containing homobiotin sulphone according to the invention.

The emulsion consisted of 10% by volume oily phase and 90% by weight aqueous phase.

The oily phase and the aqueous phase had the following constitution:

|  | % w/w |
|---|---|
| Oily phase |  |
| Castor oil polyglyceryl ester | 20 |
| Hydrophobic silica | 5 |
| Sunflower seed oil | 75 |
| Aqueous phase |  |
| homobiotin sulphone | 0.8 |
| Xanthan gum | 1 |
| Preservative | 0.3 |
| Perfume | q.s. |
| Sodium chloride (1% w/w solution) | 97.9 |

The emulsion was prepared by taking 10 parts by volume of the oily phase and to it adding slowly with stirring 90 parts by volume of the aqueous phase.

The high internal phase water-in-out emulsion so formed can be applied topically to improve skin condition generally or to alleviate greasiness and in the treatment of acne.

EXAMPLES 20 to 23

The following formulations represent lotions which can be used in the treatment of greasy and/or acneic skin.

|  | % w/w | | | |
|---|---|---|---|---|
|  | 20 | 21 | 22 | 23 |
| Hydroxyethyl cellulose | 0.4 | — | 0.4 | — |
| Absolute ethanol | 20 | 15 | 25 | 21 |
| Propane-1,2-diol | — | — | 38.4 | 38.4 |
| Butane-1,3-diol | 38.4 | 38.8 | — | — |
| Para methyl benzoate | 0.2 | 0.2 | 0.2 | 0.2 |
| homobiotin sulphone | 0.2 | — | — | — |
| bishomobiotin sulphone | — | 2 | — | — |
| trishomobiotin sulphone | — | — | 5 | — |
| bisnorbiotin sulphone | — | — | — | 1 |
| Perfume | 1 | 1 | 1 | 1 |
| Water to | 100 | 100 | 100 | 100 |

EXAMPLES 24 27

The following formulations represent lotions which can be used in the treatment of greasy and/or acneic skin.

|  | % w/w | | | |
|---|---|---|---|---|
|  | 24 | 25 | 26 | 27 |
| Ethanol | 10 | 10 | 8 | 5 |
| Propane-1,2-diol | 30 | 0 | 55 | 0 |
| Butane-1,3-diol | 0 | 30 | 0 | 55 |
| Ethyl lactate | 6 | 9 | 11 | 14 |
| norbiotin methyl ester | 0.8 | — | — | — |
| homobiotin methyl ester | — | 1.2 | — | — |
| bishomobiotin methyl ester | — | — | 1.5 | — |
| trishomobiotin methyl ester | — | — | — | 0.7 |
| perfume | q.s. | q.s. | q.s. | q.s. |
| water to | 100 | 100 | 100 | 100 |

The following examples 28 to 32 illustrate shampoos for use in the treatment of greasy hair and scalp.

EXAMPLE 28

|  | % w/w |
|---|---|
| Sodium lauryl ether sulphate (2 EO): 21% AD | 41.1 |
| Lauryl dimethylamino acetic acid betaine: 30% AD | 4 |
| Coconut fatty acid diethanolamide | 1.5 |
| Oleyl triethoxy phosphate (BRIPHOS 03D) | 1 |
| Polyglycol-polyamine condensation resin (POLYQUART H): 50% active | 1.5 |
| Preservative, colouring matter, salt | 0.58 |
| Oxybiotin sulphonic acid | 5 |
| Perfume | q.s. |
| Water to | 100 |

EXAMPLE 29

|  | % w/w |
|---|---|
| Sodium lauryl ether sulphate (2 EO): 100% AD | 12 |
| POLYQUART H: 50% active | 2.5 |
| BRIPHOS 03D | 2.5 |
| α-(2,3-ureylenecyclohexyl)butyric acid | 4 |
| Perfume | q.s. |
| Water to | 100 |

EXAMPLE 30

|  | % w/w |
|---|---|
| Monoethanolamine lauryl sulphate: 100% AD | 20 |
| POLYQUART H: 50% active | 3 |
| BRIPHOS 03D | 1.7 |

| | % w/w |
|---|---|
| Coconut diethanolamide | 5 |
| Biotin sulphone | 1 |
| Perfume | q.s. |
| Water to | 100 | pH adjusted to 6.5.

EXAMPLE 31

| | % w/w |
|---|---|
| Sodium lauryl ether sulphate (3 EO): 100% AD | 12 |
| POLYQUART H: 50% active | 0.3 |
| BRIPHOS 03D | 1 |
| α-(3,4-ureylenecyclohexyl)valeric acid | 2 |
| Perfume | q.s. |
| Water to | 100 | pH adjusted to 6.5.

EXAMPLE 32

| | % w/w |
|---|---|
| Sodium lauryl ether sulphate (2 EO): 100% AD | 12 |
| POLYQUART H: 50% active | 3 |
| BRIPHOS 03D | 1 |
| Opacifier | 9 |
| 2-oxo4-imidazolidine caproic acid | 5 |
| Perfume | q.s. |
| Water to | 100 | pH adjusted to 6.5.

EXAMPLES 33-36

The following formulations represent lotions which can be used in the treatment of greasy and/or acneic skin.

| | % w/w | | | |
|---|---|---|---|---|
| | 33 | 34 | 35 | 36 |
| Hydroxyethyl cellulose | 0.4 | — | 0.4 | — |
| Absolute ethanol | 25 | 25 | 25 | 25 |
| Propane-1,3-diol | — | — | 38.4 | 38.4 |
| Butane-1,3-diol | 38.4 | 38.8 | — | — |
| Para methyl benzoate | 0.2 | 0.2 | 0.2 | 0.2 |
| Thiazolidine | 5 | — | — | — |
| Methyl-1,3-acetyl-4-thiazolidine carboxylate | — | 0.3 | — | — |
| 1,3-propyl-2-acetyl-4-thiazolidine carboxylate | — | — | 0.8 | — |
| 2-piperidone-6-carboxylic acid hydrazide | — | — | — | 1.2 |
| Perfume | 1 | 1 | 1 | 1 |
| Water to | 100 | 100 | 100 | 100 |

EXAMPLES 37-41

The following formulations represent lotions which can be used in the treatment of greasy and/or acneic skin.

| | % w/w | | | | |
|---|---|---|---|---|---|
| | 37 | 38 | 39 | 40 | 41 |
| Ethanol | 10 | 10 | 10 | 10 | 10 |
| Propane-1,2-diol | 30 | — | 55 | — | 30 |
| Butane-1,3-diol | — | 30 | — | 55 | — |
| α-(2-carboxy-3-indol-yl) butyric acid hydrazide | 0.004 | — | — | — | — |
| 2-imidazoline-4-caproic acid hydrazide | — | 0.008 | — | — | — |
| 2-imidazoline-4-valeric acid hydrazide | — | — | 0.04 | — | — |
| Biotin sulphone | — | — | — | 0.9 | — |
| Biotin hydrazide | — | — | — | — | 0.1 |
| Perfume | q.s | q.s. | q.s. | q.s. | q.s |
| Water to | 100 | 100 | 100 | 100 | 100 |

EXAMPLES 42-47

The following Examples 42 to 47 illustrate powder compositions according to the invention which can be applied topically to moist, greasy skin.

| | % w/w | | | | | |
|---|---|---|---|---|---|---|
| | 42 | 43 | 44 | 45 | 46 | 47 |
| Chemically modified starch | 5 | — | 5 | — | 5 | — |
| Chemically modified cellulose | — | 5 | — | 5 | — | 5 |
| Boric acid | 10 | 10 | 10 | 10 | 10 | 10 |
| Zinc oxide | 5 | 5 | 5 | 5 | 5 | 5 |
| Biotin sulphone | 5 | — | — | — | — | 13 |
| Biotin sulphone methyl ester | — | 10 | — | — | — | — |
| Homobiotin sulphone | — | — | 2 | — | — | — |
| Homobiotin sulphone methyl ester | — | — | — | 4 | — | — |
| Bishomobiotin sulphone | — | — | — | — | 1 | — |
| Bishomobiotin sulphone methyl ester | — | — | — | — | — | 3 |
| Perfume | q.s. | q.s. | q.s. | q.s. | q.s. | q.s |
| Chalk | 10 | 10 | 10 | 10 | 10 | 10 |
| Talc to | 100 | 100 | 100 | 100 | 100 | 100 |

What is claimed is:

1. A method of treating human skin or hair to reduce the amount of sebum secreted onto the skin surface or hair which comprises contacting said skin or hair with an effective sebum reducng amount of a composition which comprises, at a concentration of from about 0.004% to about 10% by weight of the composition, a biotin antagonist, or a salt thereof, or mixtures thereof, which is capable of blocking the activity of the biotin-dependent enzyme acetyl-SCoA-carboxylase, involved in lipid synthesis and located in sebaceous glands of the skin; together with a carrier selected from the group consisting of liquid other than water, cream, gel, powder, lotion, emulsion, shampoo and mixtures thereof said carrier being capable of conveying said biotin antagonist to said sebaceous glands.

2. The method according to claim 1, wherein the biotin antagonist has the structure (I):

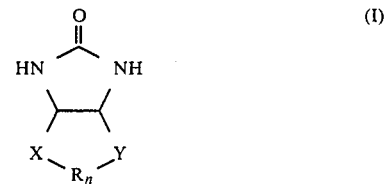

where n is zero or 1 and
when n is zero,
X is —CH₃, and
Y is —(CH₂)ₘZ and when n is 1,
R is chosen from >O, >S, >S=O or

X is >CH$_2$, and
Y is >CH(CH$_2$)$_{m-1}$Z where
m is an integer of from 1 to 8, and
Z is chosen from —CH$_2$COOH, —CH=CH-COOH, —CH(CH$_3$)COOH, —CH$_2$COOCH$_3$, —NHNH$_2$ and —SO$_3$H
provided that when n is 1, R is S, and Z is —CH$_2$COOH, then m is an integer of from 1 to 3, or 5 to 8.

3. The method according to claim 2, wherein the biotin antagonist is selected from the group consisting of trisnordesthiobiotin, bisnordesthiobiotin, nordesthiobiotin, desthiobiotin, homodesthiobiotin, bishomodesthiobiotin, trishomodesthiobiotin tetrahomodesthiobiotin, and mixtures thereof.

4. The method according to claim 2, wherein the biotin antagonist is α-methyldesthiobiotin.

5. The method according to claim 2, wherein the biotin antagonist is selected from the group consisting of trisnorbiotin sulphoxide, bisnorbiotin sulphoxide, norbiotin sulphoxide, biotin sulphoxide, homobiotin sulphoxide, bishomobiotin sulphoxide, trishomobiotin sulphoxide and mixtures thereof.

6. The method according to claim 2, wherein the biotin antagonist is selected from the group consisting of trisnorbiotin sulphone, bisnorbiotin sulphone, norbiotin sulphone, biotin sulphone, homobiotin sulphone, bishomobiotin sulphone, trishomobiotin sulphone and mixtures thereof.

7. The method according to claim 2, wherein the biotin antagonist is selected from the group consisting of trisnorbiotin, bisnorbiotin, norbiotin, homobiotin, bishomobiotin, trishomobiotin, and mixtures thereof.

8. The method according to claim 2, wherein the biotin antagonist is selected from the group consisting of α-dehydrobiotin, α-methylbiotin and a mixture thereof.

9. The method according to claim 2, wherein the biotin antagonist is selected from the group consisting of trisnoroxybiotin, bisnoroxybiotin, noroxybiotin, oxybiotin, homooxybiotin, bishomooxybiotin, trishomooxybiotin, and mixtures thereof.

10. The method according to claim 2, wherein the biotin antagonist is selected from the group consisting of trisnoroxybiotin sulphonic acid, bisnoroxybiotin sulphonic acid, noroxybiotin sulphonic acid, oxybiotin sulphonic acid, homooxybiotin sulphonic acid, bishomooxybiotin sulphonic acid, trishomooxybiotin sulphonic acid, and mixtures thereof.

11. The method according to claim 2, wherein the biotin antagonist is selected from the group consisting of trisnorbiotin methyl ester, bisnorbiotin methyl ester, norbiotin methyl ester, homobiotin methyl ester, bishomobiotin methyl ester, trishomobiotin methyl ester, tetrahomobiotin methyl ester, and mixtures thereof.

12. The method according to claim 2, wherein the biotin antagonist is selected from the group consisting of trisnorbiotin sulphone methyl ester, bisnorbiotin sulphone methyl ester, norbiotin sulphone methyl ester, biotin sulphone methyl ester, homobiotin sulphone methyl ester, bishomobiotin sulphone methyl ester, trishomobiotin sulphone methyl ester, tetrahomobiotin sulphone methyl ester, and mixtures thereof.

13. The method according to claim 2, wherein the biotin antagonist is selected from the group consisting of trisnorbiotin hydrazide, bisnorbiotin hydrazide, norbiotin hydrazide, biotin hydrazide, homobiotin hydrazide, bishomobiotin hydrazide, trishomobiotin hydrazide, and mixtures thereof.

14. The method according to claim 1, wherein the biotin antagonist has the structure:

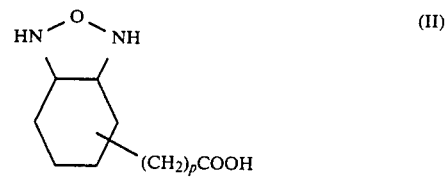

where p is an integer of from 2 to 5.

15. The method according to claim 14, wherein the biotin antagonist having the structure (II) is selected from the group consisting of:
γ-(2,3-ureylenecyclohexyl)butyric acid,
δ-(2,3-ureylenecyclohexyl)valeric acid,
γ-(3,4-ureylenecyclohexyl)butyric acid,
δ-(3,4-ureylenecyclohexyl)valeric acid, and mixtures thereof.

16. The method according to claim 1, wherein the biotin antagonist is selected from the group consisting of:
2-oxo-4-imidazolidine caproic acid, thiazolidine,
methyl-1,3-acetyl-4-thiazolidine carboxylate,
1,2-propyl-2-acetyl-4-thiazolidine carboxylate methyl ester, and its hydrazide,
2-piperidone-6-carboxylic acid hydrazide,
γ-(2-carboxy-3-indolyl)butyric acid hydrazide,
2-imidazoline-4-carboxylic acid hydrazide,
2-imidazoline-4-caproic acid hydrazide,
2-imidazoline-4-valeric acid hydrazide,
ureylenetetrahydrofuryl aliphatic sulphonic acids,
benzyl thio esters,
semicarbazides of biotin,
bishydrazides of suberic acid and sebacic acids, and mixtures thereof.

17. The method according to claim 1, wherein the carrier other than water is a C$_1$ to C$_4$ alkanol selected from the group consisting of ethanol, propane-1-ol, propane-2-ol and mixtures thereof.

18. The method according to claim 1, wherein the carrier is a powder selected from the group consisting of chalk, talc, fullers earth, kaolin, starch, gums, colloidal silicon dioxide, sodium polyacrylate, tetra-alkyl arylammonium smectite, tri-alkyl arylammonium smectite, chemically modified magnesium aluminum silicate, organically modified montmorillonite clay. hydrated aluminum silicate, fumed silica, carboxyvinyl polymer, sodium carboxymethyl cellulose, and ethylene glycol monostearate.

19. The method according to claim 1, which further comprises water.

* * * * *